United States Patent [19]

Labun et al.

[11] Patent Number: 5,748,845
[45] Date of Patent: May 5, 1998

[54] FES METHOD AND SYSTEM FOR CONTROLLING THE MOVEMENT OF A LIMB

[75] Inventors: Nicholas M. Labun, Chicago; Thomas J. McClaughry, Hoffman Estates; Shay-Ping T. Wang, Long Grove, all of Ill.

[73] Assignee: Motorola, Inc., Schaumburg, Ill.

[21] Appl. No.: 509,555

[22] Filed: Jul. 31, 1995

[51] Int. Cl.$^6$ .............................. G06F 15/18; A61N 1/00
[52] U.S. Cl. .................................................. 395/20; 607/66
[58] Field of Search ................................ 395/20, 22, 11; 128/419, 421; 364/148

[56] References Cited

U.S. PATENT DOCUMENTS

| | | | |
|---|---|---|---|
| 4,697,808 | 10/1987 | Larson et al. | 272/70 |
| 5,016,635 | 5/1991 | Graupe | 128/421 |
| 5,092,329 | 3/1992 | Graupe et al. | 128/419 |
| 5,112,296 | 5/1992 | Beard et al. | 602/28 |
| 5,455,890 | 10/1995 | Wang | 395/22 |
| 5,546,302 | 8/1996 | Wang et al. | 364/148 |
| 5,550,732 | 8/1996 | Wang et al. | 364/148 |
| 5,583,964 | 12/1996 | Wang | 395/11 |

OTHER PUBLICATIONS

"EMG Pattern Analysis for Patient–Responsive Control of FES in Paraplegics for Walker–Supported Walking" by Daniel Graupe, IEEE Transactions on Biomedical Engineering, vol. 36, No. 7, Jul. 1989.

"A Functional Electrical Stimulation Exercise System Designed to Increase Bone Density in Spinal Cord Injured Individuals" by Mark S. Malagodi, Martin W. Ferguson–Pell, and Robert D. Masiello, IEEE Transactions on Rehabilitation Engineering, vol. 1 No. 4, Dec. 1993.

"Comparison of Natural and Artificial Control of Movement" by Arthur Prochazka, IEEE Transactions on Rehabilitation Engineering, vol. 1, No. 1, Mar. 1993.

"Adaptive Approach to Functional Electrical Stimulation" by G.A. Pajunen and W. Price, Proceedings of the 27th Conference on Decision and Control, Austin, Texas, Dec. 1988.

"A Custom–Chip–Based Functional Electrical Stimulation System" by Richard Broberg and Allyn Hubbard, IEEE Transactions on Biomedical Engineering, vol. 41, No. 9, Sep. 1994.

"Task–Dependent Scheduling of Feedback Gains in Animal Motor Systems: Too Much, Too Soon for FES Control?" by Arthur Prochazka; IEEE Engineering in Medicine and Biology; Dec. 1992.

"Finite State Control of FES Systems: Application of AI Inductive Learning Techniques" by Craig A. Kirkwood, Brian J. Andrews; IEEE Engineering in Medicine & Biology Society 11th Annual International Conference; 1989.

"Control of Locomotion by Multi–Channel Portable FES System" by M. Ichie, T. Handa, Y. Handa, N. Hoshimiya, A. Naito, K. Ushikoshi, H. Fukamachi, M. Yajima, T. Ito; IEEE Engineering in Medicine & Biology Society 11th Annual International Conference; 1989.

"EMG as a Feedback Signal in Surface FES Applications: Issues and Preliminary Results" by W.K. Durfee, J.T. Dennerlein; IEEE Engineering in Medicine & Biology Society 11th Annual International Conference; 1989.

(List continued on next page.)

Primary Examiner—Robert W. Downs
Assistant Examiner—Sanjiv Shah
Attorney, Agent, or Firm—Bruce E. Bruckman; Jeffrey G. Toler

[57] ABSTRACT

A system for controlling the movement of at least one limb of a person's body includes an interface unit in communication with the person's body for receiving an input signal. A polynomial processor generates a control signal as a polynomial function of the at least one input signal. A generator generates a functional electrical stimulation signal. A plurality of electrodes stimulates the movement of the at least one limb by introducing the functional electrical stimulation signal to the at least one of a plurality of inactive muscles.

11 Claims, 5 Drawing Sheets

OTHER PUBLICATIONS

"Development of Second Generation FES System for Practical" by K. Okubo, N. Hoshimiya, Y. Handa; IEEE Engineering in Medicine & Biology Society 11th Annual International Conference; 1989.

"Studies on Control Commands for FES in the Paralyzed Extremities" by T. Handa, Y. Handa, M. Ichie, J. Kameyama, H. Takahashi, M. Yajima, T. Itoh, N. Hoshimiya; IEEE Engineering in Medicine & Biology Society 11th Annual International Conference; 1989.

"Lower Extremity Functional Electrical Stimulation with Spinal Cord Injured Subjects at the Ohio State University" by Randall S. Swartz, Herman R. Weed, William S. Pease, Elaine F. Betts; IEEE Engineering in Medicine & Biology Society 11th Annual Int'l Conference; 1989.

"A Systems Approach to Physician Prescribed F.E.S. Ambulation" by C.A. Phillips, D. Hendershot, S. Kizayat, H. Granek, M. Granek; IEEE Engineering in Medicine & Biology Society 11th Annual International Conference; 1989.

"A Four-Channel IBM PC/AT Compatible Biphasic Pulse Generator for Nerve Stimulation" by Paul M. Meadows, Donald R. McNeal; IEEE Transactions on Biomedical Engineering; vol. 36, No. 7; Jul. 1989.

"Development of Percutaneous Intramuscular Electrode for Multichannel FES System" by Yasunobu Handa, Nozomu Hoshimiya, Yasutaka Iguchi, Takashi Oda; IEEE Transactions on Biomedical Engineering; vol. 36, No. 7; Jul. 1989.

"Evaluation of FES Control System Employing Adaptive and PI Controllers" by N. Itakura, K. Fujita, K. Kubo, Y. Iguchi, H. Minamitani; IEEE Engineering in Medicine & Biology Society 10th Annual International Conference; 1988.

"Development of a Portable FES System for the Paralyzed Extremities" by a Naito, Y. Handa, M. Yajima, M. Tanaka, S. Ishikawa, K. Okubo, N. Hoshimiya; IEEE Engineering in Medicine & Biology Society 10th Annual International Conference; 1988.

"FES Controlled Ambulation with Surface Electrodes and No Orthotics" by Brenda Scoggins, Richard Scopp, Judith B. Walker, Michael Morse; IEEE Engineering in Medicine & Biology Society 10th Annual International Conference; 1988.

"The EMS-RGO: A Physician Prescribable FES Ambulation Exercise System" by Chandler A. Phillips, Debra M. Hendershot; IEEE Engineering in Medicine & Biology Society 10th Annual International Conference; 1988.

"A Voice Controlled FES System for Restoring Hand Functions in Quadriplegics" by L. Bohs, J. McElhaney, E. Cooper, M. Joost, D. Han, F. Clippinger; IEEE Engineering in Medicine & Biology Society 10th Annual International Conference: 1988.

"A Neural Network for Noninvasive Decomposition of Surface EMG Signals Using Gaussian Nodes" by Ruey–wen Liu, Qiu Huang, Daniel Graupe; IEEE 1990 International Symposium on Circuits and Systems, May 1–3, 1990.

"Identification of Nonstationary Models with Application to Myoelectric Signals for Controlling Electrical Stimulation of Paraplegics" by Alvin Todd Moser, Daniel Graupe; IEEE Transactions on Acoustics, Speech and Signal Processing; vol. 37, No. 5; May 1989.

"Control of Electrically–Stimulated Walking of Paraplegics Via Above– and Below–Lesion EMG Signature Identification" by Daniel Graupe, Kate H. Kohn, Stavros P. Basseas; IEEE Transactions on Automatic Control; vol. 34, No. 2; Feb. 1989.

"EMG Signal Discrimination for Controlling Walking Functions in Paraplegics Under Electrical Stimulation" by Stavros P. Basseas and Daniel Graupe, IEEE 1988 International Symposium on Circuits and Systems, Jun. 7–9, 1988.

"EMG as an Indicator of Fatigue in Isometrically Fes–Activated Paralyzed Muscles" by J. Mizrahi, M. Levy, H. Ring, E. Isakov, A. Liberson; IEEE Transactions on Rehabilitation Engineering; vol. 2, No. 2; Jun. 1994.

"Neural Network Generation of Muscle Stimulation Patterns for Control of Arm Movements" by Ning Lan, Huan–Qing Feng, Patrick E. Crago; IEEE Transactions on Rehabilitation Engineering; vol. 2, No. 4; Dec. 1994.

"Application of External Forces on an Active Orthosis" by Aysin Yeltekin, Max Corbin; International Biomedical Engineering Days; 1992.

"Hybrid Assistive System—The Motor Neuroprosthesis" by Dejan Popovic, Rajko Tomovic, Laszlo Schwirtlich; IEEE Transactions on Biomedical Engineering; vol. 36, No. 7; Jul. 1989.

"Hybrid FES Orthosis for Standing Up in Paraplegia" by Chifuyu Komiyama, Eiichi Saito, Yutaka Tomita, Satoshi Honda; IMTC '94; May 10–12, 1994.

"Control of Hybrid FES System for Restoration of Paraplegic Locomotion" by Taro Ohashi, Goro Obinata, Yoichi Shimada, Kunio Ebata; IEEE International Workshop on Robot and Human Communication; 1993.

"Artificial Neural Network Control of FES in Paraplegics for Patient Responsive Ambulation" by Daniel Graupe et al., IEEE Transactions on Biomedical Engineering, vol. 42, No. 7, Jul. 1995.

Graupe et al., Control of Electrically Stimulated Walking of Paraplegics Via Above– and Below–lesion EMG Signature Identification, IEEE Transaction on Automatic control vol. 34, No. 2, pp. 130–138, Feb. 1989.

Lan et al., Neural network generation of muscle stimulation patterns for control of arm movements, IEEE Transactions on Rehabilitation Engineering vol. 2, pp. 213–224, Dec. 1994.

Haugland et al., Artifact–free sensory nerve signals obtained from cuff electrodes during functional electrical stimulation of nearby muscles, IEEE Transactions on Rehabilitation Engineering vol. 2, pp. 37–40, Mar. 1994.

Mizrahi et al., EMG as an indicator of fatigue in isometrically FES–activated paralyzed muscles, IEEE Transactions on Rehabilitation Engineering, vol. 2, pp. 57–65, Jun. 1994.

Popovic et al., Sensory nerve recording for closed–loop control to restore motor functions, IEEE Transactions on Biomedical Engineering, Oct. 1993.

FES METHOD AND SYSTEM FOR CONTROLLING THE MOVEMENT OF A LIMB

RELATED INVENTIONS

The present invention is related to the following inventions which are assigned to the same assignee as the present invention:

(1) "Artificial Neuron and Method of Using Same", having U.S. Pat. No. 5,390,136, filed Jun. 14, 1993;

(2) "Auto Tuning Controller and Method of Use Therefor" having Ser. No. 08/268,395, filed Jun. 30, 1994;

(3) "Auto-Scaling Controller and Method of Use Therefor" having U.S. Pat. No. 5,633,987, filed Jul. 28, 1994; and (4) "Cascade Tuning Controller and Method of Use Therefor" having Ser. No. 08/288,379, filed Aug. 10, 1994.

(5) "Controller for Nonlinear Systems and Method for Use Thereof", having U.S. Pat. No. 5,550,732, filed Dec. 19, 1994.

(6) "Method of Programming a Polynomial Processor", having Ser. No. 08/358,278, filed Dec. 19, 1994.

(7) "Polynomial controller for nonlinear systems and methods of use thereof," having U.S. Pat. No. 5,546,302, filed Dec. 19, 1994.

(8) "Active orthosis method and system for controlling the movement of a limb," having Ser. No. 08/509,564.

(9) "Hybrid FES and active orthosis method and system for controlling the movement of a limb," having Ser. No. 08/509,556.

The subject matter of the above-identified related inventions is hereby incorporated by reference hereto into the disclosure of this invention.

FIELD OF THE INVENTION

The present invention relates generally to controllers and, in particular, to controllers for controlling the movement of inactive limbs.

BACKGROUND OF THE INVENTION

More than one-quarter of a million people currently have impaired use of their limbs due to injuries to their spinal cords. This impaired limb use, besides creating mental and physical challenges to the patient also can generate muscular atrophy, loss of bone mineral content, decubitus ulcers, urinary tract infections, muscles spasticity, impaired circulation, and reduced heart and lung capacity.

Prior art control systems have attempted to correct many of these problems by providing motion of the impaired limb based upon the introduction of functional electrical stimulation signals to the muscles of the limb. Alternative active orthosis systems provide an exoskeletal support structure that is driven by electrical motors or hydraulic systems.

While providing a great advance in the medical prostheses, these prior art approaches suffer from an inaccurate and coarse form of control that is unsuitable for many patients. There is a need for a control system that provides a greater fluidity of limb motion.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DETAILED DESCRIPTION OF A PREFERRED EMBODIMENT

Figure 1:
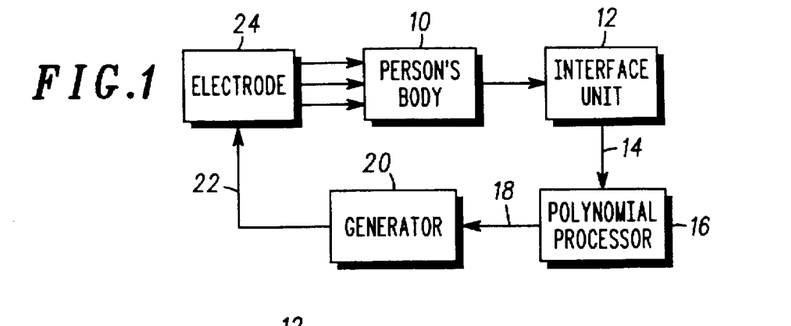
FIG. 1 illustrates a block diagram representation of a system in accordance with an embodiment of the present invention for controlling the motion of at least one limb of a person's body.

FIG. 1 illustrates a block diagram representation of a system in accordance with an embodiment of the present invention for controlling the motion of at least one limb of a person's body. Person's body 10 has a limb with a plurality of inactive muscles. It is assumed that the person, due to any one of a number of medical reasons has limited use of the limb and thus, has limited or no control of the plurality of inactive muscles of the limb through the operation of the person's body.

Interface unit 12, in communication with the person's body, generates an input signal 14. This input signal 14 can be generated in many ways. For instance, input signal 14 can be generated by one or more sensors that monitor the person's biological functions or by one or more switches that provide the person the ability to more directly provide input to the system. The input signal 14 can be represented by either a scalar function of time or a vector function of time depending on the configuration and make-up of the interface unit 12.

Polynomial processor 16 is responsive to the input signal 14 and generates a control signal 18 as a polynomial function of the input signal. The use of this sophisticated device allows for the system to provide more accurate control and faster response times to allow the limb motion that is more complex than traditional control systems and with greater fluidity of motion of the effected limb. The operation of a specific embodiment of the polynomial processor 16 and a method for programming this processor is provided in conjunction with FIGS. 4 and 5. In particular, the introduction of the nonlinear terms of the polynomial allow for greater diversity in the determination of a control solution. Further, the great speed that the control signal can be calculated by the parallel network configuration of the polynomial processor that is described herein allow for more rapid control response.

Generator 20 is responsive to the control signal 18 and generates a functional electrical stimulation (FES) signal 22. The FES signal is introduced to a plurality of electrodes 24, coupled to at least one of the plurality of inactive muscles of the person's body 10, for stimulating the motion. In effect, the FES signals provide current pulses to produce controlled muscle contractions in inactive muscles. These electrodes can be placed percutaneously via implants under the skin of the person's body 10. Alternatively the electrodes can be placed transcutaneously outside of the skin of the person's body 10.

In an embodiment of the present invention, polynomial processor 16 and generator 20 work in combination to provide a sequence of FES signals that have the effect of providing a sequence of desired movements of the inactive muscle or muscles. In this manner, complex patterns of motion such as reaching, standing, walking etc. can be accomplished through the control of a plurality of muscles in a sequence that emulates the normal motion of an unimpaired person.

Figures 2, 3:
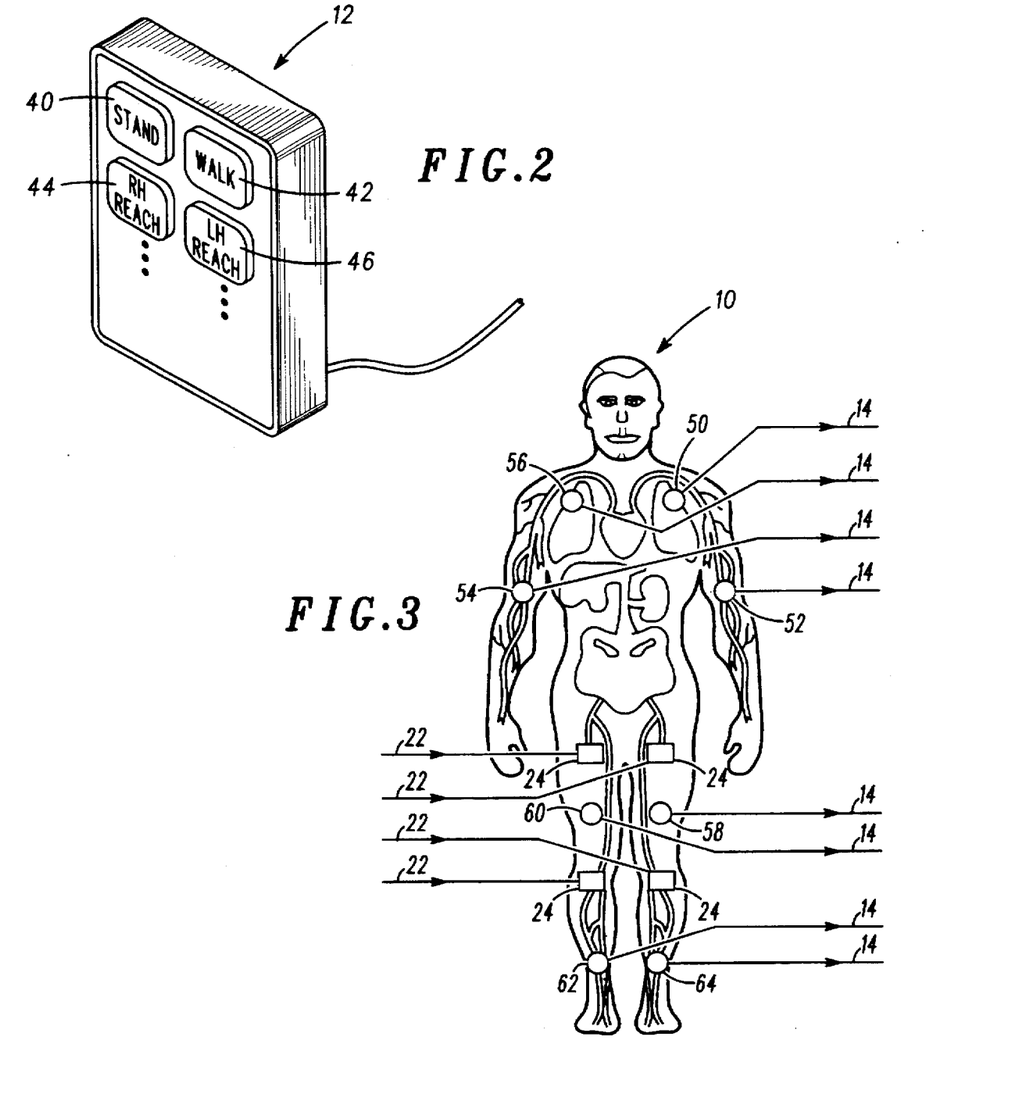
FIG. 2 shows a perspective view of the interface unit 12 in accordance with an embodiment of the present invention.
FIG. 3 shows a schematic representation of a person's body in accordance with an embodiment of the present invention.

FIG. 2 shows a perspective view of the interface unit 12 in accordance with an embodiment of the present invention. In this embodiment, interface unit 12 includes a plurality of buttons 40–46 that are each coupled to a separate switch (not expressly shown). The depression of button 40, for instance, closes a switch contact that generates an input signal to polynomial processor 16 indicative of the desire of the person to stand. Similarly buttons 42–46 correspond to other complex patterns of motion such as reaching with the person's right or left hand or walking. In instances where the person does not have the full use of his or her hands, the buttons 40–46 of interface unit 12 can be designed to be activated by touch of a chin, nose or other portion of the person's body 10. Further, buttons 40–46 of interface unit 12 can be designed to be activated by touch of a wand or stylus held by the person in his or her teeth. In an alternative embodiment of the present invention, interface unit 12 includes a microphone and speech recognition system for monitoring the voice of the person and for providing input signals 14 in response to recognized commands such as "stand", "walk" or "reach".

FIG. 3 shows a schematic representation of a person's body in accordance with an embodiment of the present invention. Person's body 10 is attached with a plurality of electrodes 24 that are provided a like plurality of FES signals 22. In this embodiment of the present invention, the person is paraplegic, that is, the person is paralyzed from the waist down. The electrodes 24 provide current pulses to the inactive muscles of the legs so as to stimulate complex patterns of motion such as standing, balancing, and walking.

FIG. 3 also a plurality of sensors 52–64 used in accordance with an alternative embodiment of the present invention, In this embodiment sensors 50–64 provide the function of interface unit 12 of generating a plurality of input signals 14. Input signals 14 from sensors 50–56, in contact with the person's body 10, provide empirical electromyographic signature data from non-paralyzed portions of the person's body 10. In this manner, the natural response of the non-paralyzed muscle sites can be used to trigger the initiation of movement in the paralyzed limbs. For instance, the action of the chest muscles of the person's body 10 while trying to stand could be used to trigger the control of the person's paralyzed legs via generated FES signals so as to stimulate the standing response. In addition, sensors 50–56 can be used to monitor other biological parameters of the person's body 10, such as skin resistivity, perspiration levels, heart-rate, breathing-rate etc. which are useful to the motion control.

Input signals 14 from sensors 58–64 in contact with inactive muscles of the legs generate input signals 14 that provide data on the fatigue of these inactive muscles. In this fashion, fatigue feedback (that is normally felt by a non-paralyzed person) can be incorporated into the control of the person's body so as to take appropriate control action. Appropriate control action may include ceasing the movement until the fatigue passes or modifying the control based on the presence of fatigue.

Figure 4:
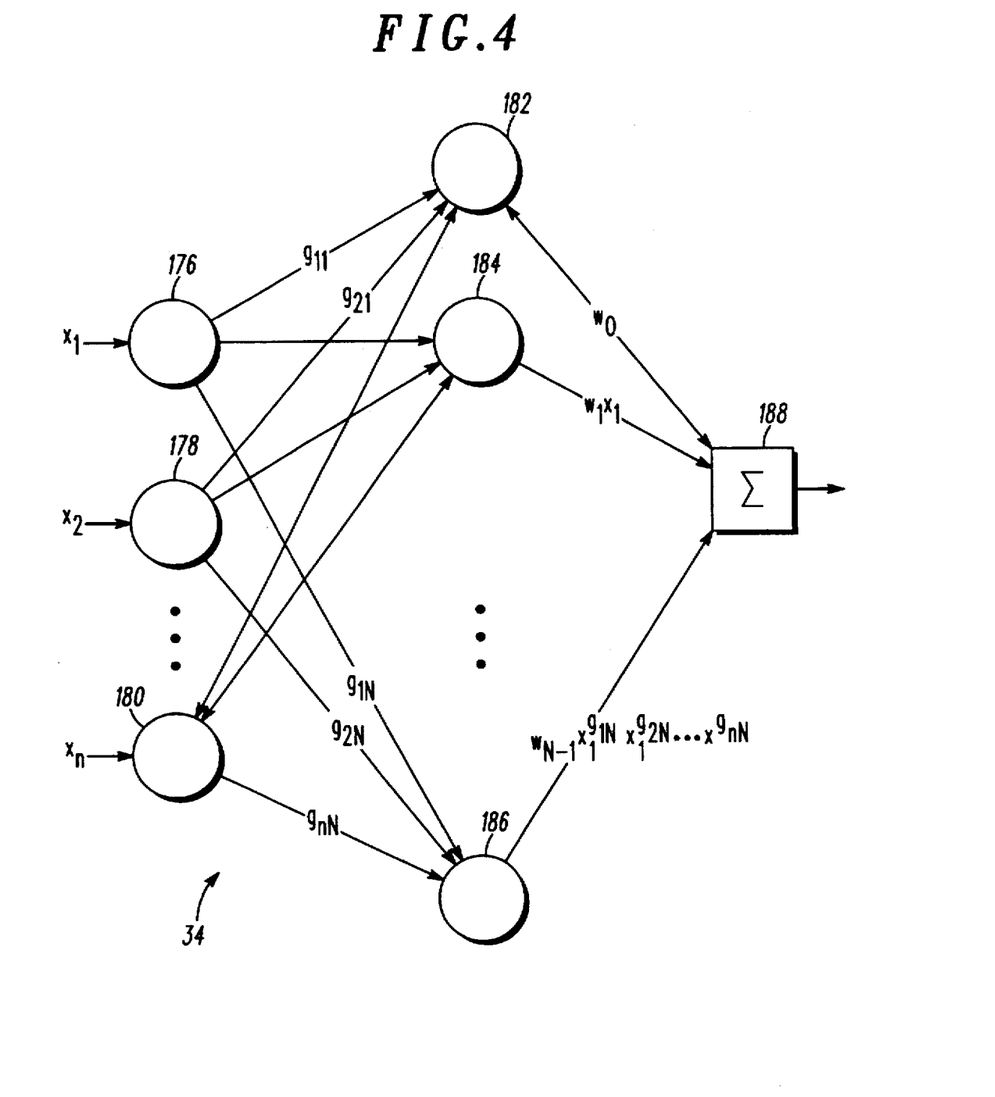
FIG. 4 shows a schematic representation of the polynomial processor used in an embodiment of the present invention.

FIG. 4 shows a schematic representation of the polynomial processor used in an embodiment of the present invention. This polynomial processor 16 calculates output command signals as a polynomial function of one or more control input signals. A plurality of control input signals, $x_1$, $x_2$, ..., $x_n$ are fed to input nodes 176, 178, ... 180 of an input layer. The output of each input node 176, 178, ... 180 in the input layer is distributed at least one processing element of a hidden layer (of which only processing elements 182, 184, 186 are shown). Each processing element applies a gating function to each of the control inputs to produce a corresponding gated input. Any given processing element may apply a different gating function to each different control input it receives. For example, processing element 182 applies a gating function ($g_{11}$) to the control input it receives from input node 176; it applies a gating function ($g_{21}$) to the control input it receives from input node 178; and so forth. The gated inputs are multiplied together by a multiplier in the processing element to form a product, which is then multiplied by a control coefficient $w_{i-1}$ to form the ith term of the polynomial. The ith term of the polynomial is added to the other, similarly calculated, terms by summer 188 to produce the control output y.

For example, in FIG. 4 processing element 182, which happens to be responsible for generating the first polynomial term, multiplies its gated inputs together to form a product (which happens to be one because in this case the gating functions $g_{11}$, $g_{21}$, ... $g_{n1}$ are all 0), which is multiplied by a control coefficient $w_o$ to produce a corresponding output $w_o$. Processing element 184, which happens to be responsible for generating the $w_1$ $x_1$ term of the polynomial, multiplies its gated inputs together to form a product (which happens to be $x_1$ because in this case the gated functions are all 0 except for the gating function that is applied to the $x_1$ output of the input node 176), which is multiplied by a control coefficient $w_1$ to produce a corresponding output $x_1$ $w_1$. In like fashion, processing element 186 produces an output $w_{n-1}$ $x_1$ to the power of $g_{1n}$, $x_2$ to the power of $g_{2n}$, ..., $x_n$ to the power of $g_{nN}$. The outputs of processing elements 182, 184, ... 186 are summed together by a suitable summing means or function, such as summer 188, in an output layer to produce the output command signal y of the processor as follows:

$$y = \sum_{i=1}^{m} w_{i-1} x_{1gl_i} x_{2g2_i} \ldots x_{ng n_i} \quad (1)$$

where m is an integer which represents the number of terms in the polynomial.

Figure 5:
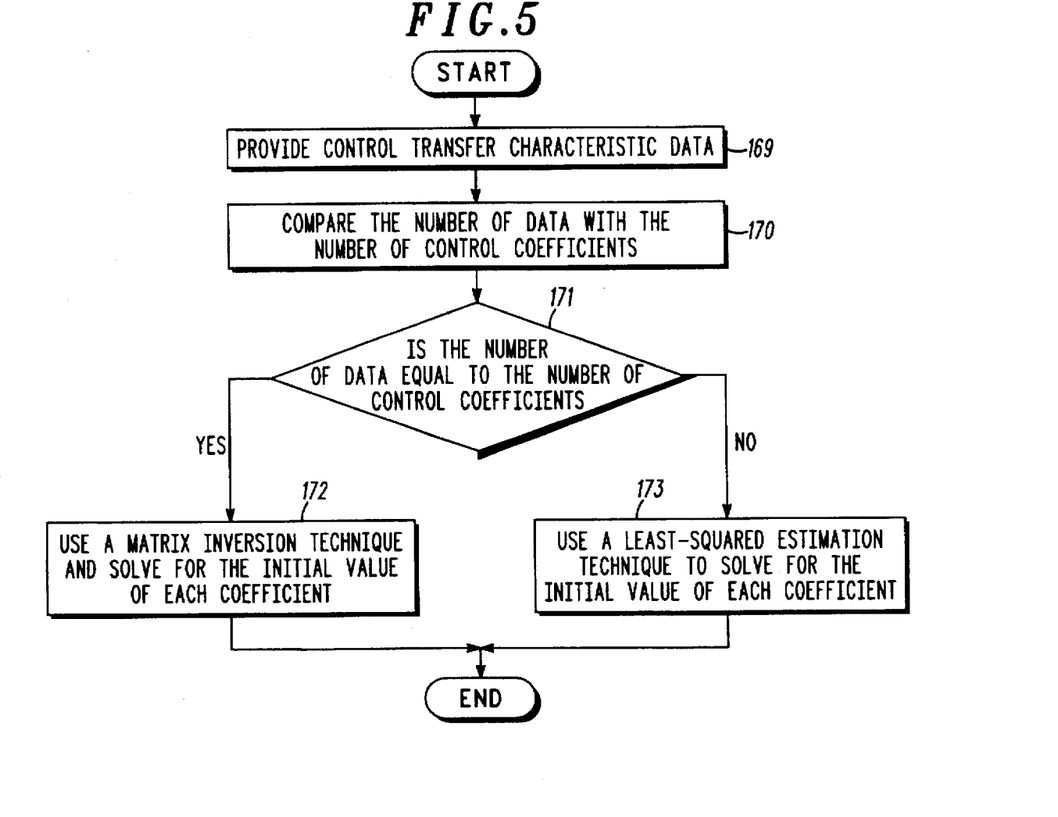
FIG. 5 shows a flow chart representation of a method of determining control coefficients for a processor in accordance with FIG. 4 in one embodiment of the present invention.

FIG. 5 shows a flow chart representation of a method of determining control coefficients for a processor in accordance with FIG. 4 in one embodiment of the present invention. First, regarding box 169, control transfer characteristic data that represent the desired control output values as a function of the input values are provided. Next, regarding box 170, the number of data is compared with the number of control coefficients. Regarding decision box 171, if the number of data equal the number of control coefficients, the procedure goes to box 172 which indicates that a matrix inversion technique is used to solve for the initial value of each coefficient. If, on the other hand, the number of data is not equal to the number of control coefficients, the procedure goes to box 173, which indicates that a least squares estimation technique is used to solve for the initial value of each coefficient.

In a preferred embodiment of the present invention, the control transfer characteristic data are generated based upon the movements of a unimpaired limb. In particular, for an active orthosis embodiment, an input/output data set can be generated by reading a plurality of example input signals and reading the corresponding drives signals off a series of drive motors that are acting as tachometers. In this case the motion of the unimpaired person's limbs drives the external bracing and the velocity of the drive motors generates a voltage signal in proportion to velocity. A similar arrangement can be used for the FES embodiment of the present invention. Example input signals can be read and recorded, the unimpaired person's limbs can be moved in response to the input and the actual muscle stimulation signals (generated by the body so as to generate the motion of the limb) can be read and recorded to generate the input/output data necessary for forming the control transfer characteristic.

While a preferred embodiment is described herein, one with ordinary skill-in-the-art will recognize that other suitable estimation techniques, for example, extended least squares, pseudo inverse, Kalman filtering techniques, maximum likelihood techniques, Bayesian estimation, polynomial splines, and alike, could likewise be used to fit the control polynomial to the transfer characteristic data.

Figure 6:
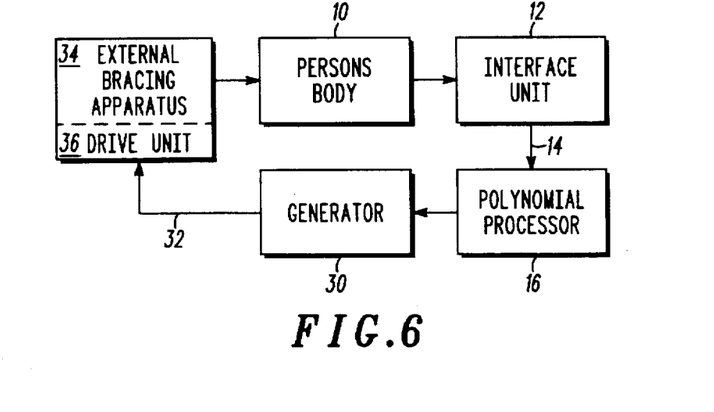
FIG. 6 illustrates a block diagram of the system in accordance with an alternative embodiment of the present invention.

FIG. 6 illustrates a block diagram of the system in accordance with an alternative embodiment of the present invention. Elements 10–18 correspond to like elements previously discussed. In this embodiment of the present invention an active orthosis system for controlling the motion of at least one limb of a person's body 10 is presented that uses an external bracing apparatus 34. This external bracing apparatus 34 provides support to the limb and may include at least one drive unit 36, a cybernetic actuator that drives the motion of external bracing apparatus in response to a drive signal 32. Generator 30, responsive to the control signal 18, generates the drive signal 32 for the drive unit 36. In an alternative embodiment of the present invention, the drive unit consists of an actuated clutch mechanism that selectively "freezes" or restricts the motion of a joint of the external bracing apparatus in response to the drive signal. In this fashion the external bracing apparatus can provide more rigid support in some selected instances such as the act of holding still while standing.

The system of FIG. 6 has the advantage that it need not rely upon the stimulation of inactive muscles of person's body 10 and it can retain or support the position of persons body 10. In some cases, the inactive muscles of person's body 10 may be unsuitable for stimulation by the methods previously described. In this case, the system of FIG. 6 provides an alternative solution to the control of limbs including these inactive muscles.

Figure 7:
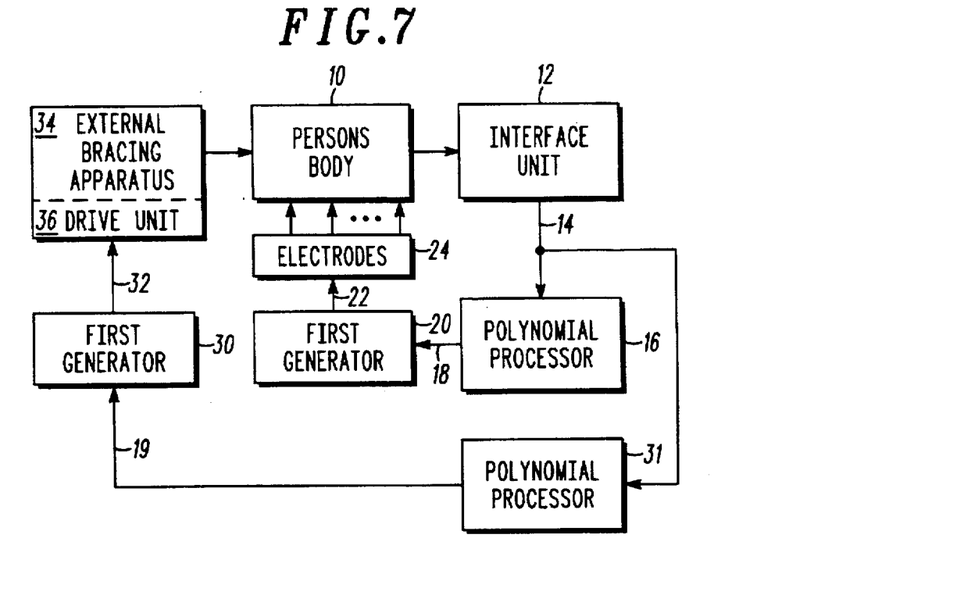
FIG. 7 illustrates a block diagram representation of a hybrid system in accordance with a further embodiment of the present invention.

FIG. 7 illustrates a block diagram representation of a hybrid system in accordance with a further embodiment of the present invention. This system presents a hybrid between the active orthosis system of FIG. 6 and the FES system of FIG. 1. A second polynomial processor 31 calculates a control signal 19 based on the input signal 14. First generator 20 generates FES signals in response to the control signal 18. Second generator 30 generates drive signals in response to control signal 19. In this fashion, polynomial processors 16 and 31 synchronously control the operation of both the inactive muscles and the external bracing apparatus so as to simultaneously control the motion of the limb from these two sources.

Figure 8:
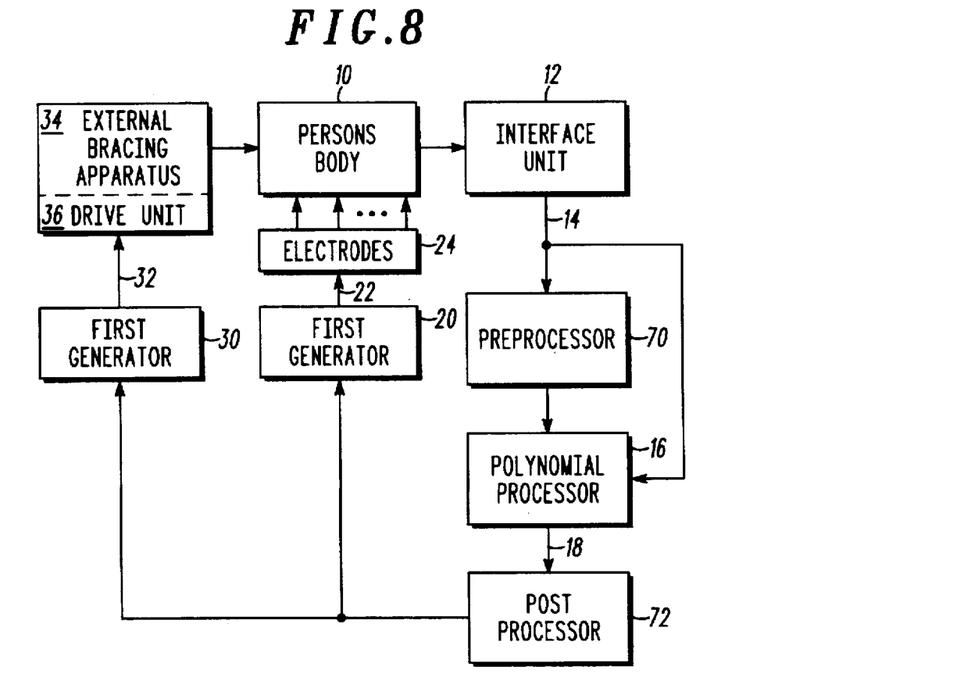
FIG. 8 illustrates a block diagram representation of a system in accordance with an additional embodiment of the present invention.

FIG. 8 illustrates a block diagram representation of a system in accordance with an additional embodiment of the present invention. In addition to the elements of FIG. 7, this system includes a preprocessor 70 and a post processor 72. In this embodiment of the present invention, a single polynomial processor 16 is used to generate a single control signal 18.

Preprocessor 70 preprocesses input signal 14 prior to its introduction to polynomial processor 16. In an embodiment of the present invention, preprocessor 70 filters input signal 14. In alternative embodiments of the present invention, high-pass, low-pass, band-pass or notch filtering or any combination thereof can be performed on input signal 14 so as to condition this signal or signals prior to processor. In an embodiment where input signal 14 is a vector quantity comprising a plurality of individual signals, these filters can be customized to each individual signal to provide the appropriate conditioning. While the operation of preprocessor 70 has been described in terms of a filtering operation, other preprocessing operations such as limiting, dead-band, sample and hold, etc, can likewise be performed and should be considered to be within the broad scope of the term preprocessing.

Post processor 72 processes the control signal 18 prior to its introduction to either the generator 20 or the generator 30. In one embodiment of the post processor 72, the control signal 18 is compared with a control signal threshold. If the control signal is above a threshold a first control signal is generated. If however, the control signal is below the threshold, a second control signal is generated. While the operation of post processor 72 has been described in terms of a comparing operation, other post processing operations such as filtering, limiting, dead-band, sample and hold, etc, can likewise be performed and should be considered to be within the broad scope of the term post processing. In an alternative embodiment of the present invention, post processor 72 generates two different signals, a first signal for input to the first generator 20, and a second signal for input to the second generator 30. In this fashion potentially distinct requirements of the two generators can be accommodated.

Figure 9:
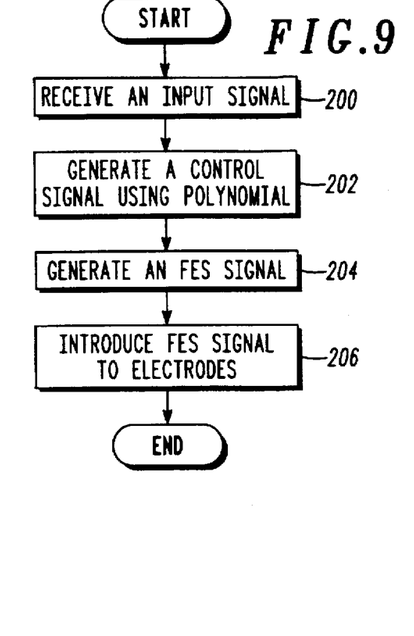
FIG. 9 presents a flowchart representation of a method used in conjunction with one embodiment of the present invention.

FIG. 9 presents a flowchart representation of a method used in conjunction with one embodiment of the present invention. This method of operation can be used in conjunction with the system of FIG. 1. The method begins in step 200 by receiving an input signal from an interface unit in communication with the person's body. A control signal is generated as a polynomial function of at least one input signal as shown in step 202. A functional electrical stimulation signal is generated based on the control signal as shown in step 204 and the motion of at least one limb is stimulated by introducing the functional electrical stimulation signal to at least one of the plurality of inactive muscles as shown in step 206.

Figure 10:
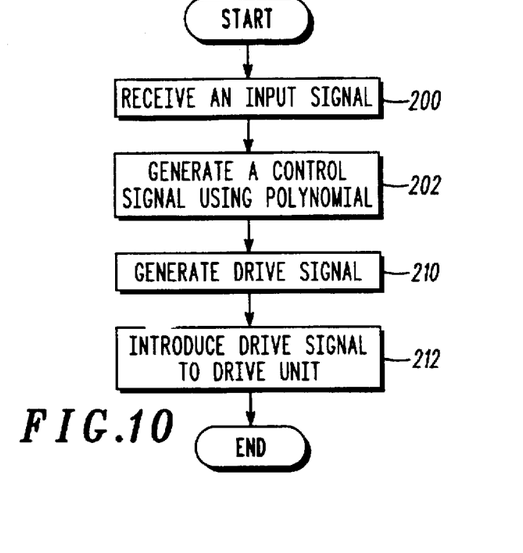
FIG. 10 presents a flowchart representation of a method used in conjunction with an alternative embodiment of the present invention.

FIG. 10 presents a flowchart representation of a method used in conjunction with an alternative embodiment of the present invention. This method is for controlling the motion of a least one limb of a person's body using a external bracing apparatus having at least one drive unit that drives the motion of external bracing apparatus in response to a drive signal. In particular, this method can be used in conjunction with the system of FIG. 6. Like reference numerals correspond with steps common to the method of FIG. 9. Step 210 includes generating the drive signal based on the control signal. The at least one limb is moved by introducing the drive signal to the drive unit as shown in step 212.

Figure 11:
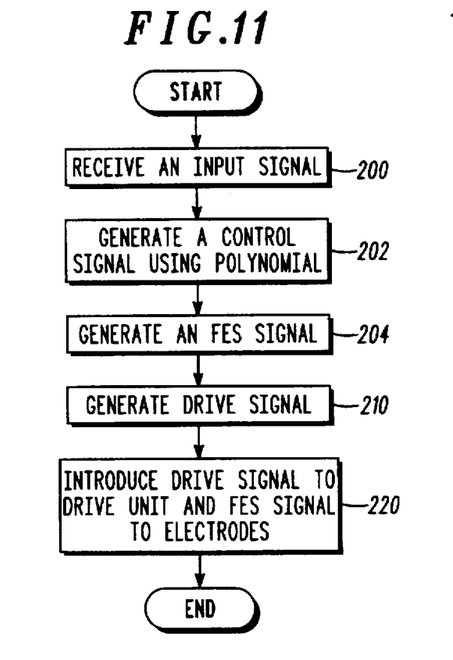
FIG. 11 presents a flowchart representation of a method used in conjunction with a further embodiment of the present invention.

FIG. 11 presents a flowchart representation of a method used in conjunction with a further embodiment of the present invention. This method is for controlling the motion of at least one limb of a person's body using an external bracing apparatus having at least one drive unit that drives the motion of external bracing apparatus in response to a drive signal, the limb having a plurality of inactive muscles, the person having limited control of the plurality of inactive muscles of at least one limb through the operation of the person's body. In particular, this method can be used in conjunction with the system of FIG. 7. Like reference numerals correspond with steps common to the method of FIG. 9 & 10. This method includes step 220 for moving the at least one limb by introducing the functional electrical stimulation signal to at least one of the plurality of inactive muscles and by introducing the drive signal to the drive unit.

Figure 12:
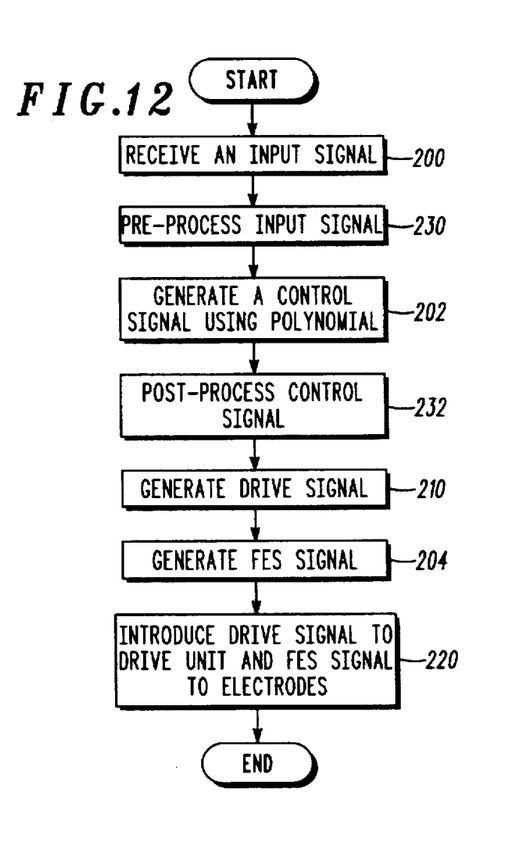
FIG. 12 presents a flowchart representation of a method used in conjunction with an additional embodiment of the present invention.

FIG. 12 presents a flowchart representation of a method used in conjunction with an additional embodiment of the present invention. This method is for controlling the motion of at least one limb of a person's body using an external bracing apparatus having at least one drive unit that drives the motion of external bracing apparatus in response to a drive signal, the limb having a plurality of inactive muscles, the person having limited control of the plurality of inactive muscles of at least one limb through the operation of the person's body. In particular, this method can be used in conjunction with the system of FIG. 8. Like reference numerals correspond with steps common to the method of FIG. 9, 10 & 11. In addition, this method includes step 230 of preprocessing the input signal prior to the step of generating a control signal. The control signal is also post processed as shown in step 232.

It should be obvious to one of ordinary skill in the art that many of the elements used in the various embodiments of the present invention are well suited for implementation on a processor such as a microprocessor, a digital signal processor or a micro controller. Likewise these elements could be performed in hardware by a custom integrated circuit, ASIC, programmable logic array or similar devices.

While specific embodiments of the present invention have been shown and described, it will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A limb stimulation system comprising:

an interface unit in communication with at least one limb of a person's body;

a first parallel processor responsive to the interface unit;

a second parallel processor responsive to the interface unit;

a first generator responsive to the first parallel processor;

a second generator responsive to the second parallel processor;

at least one electrode responsive to the first generator, the at least one electrode in communication with at least one muscle of the person's body;

a drive unit responsive to the second generator; and a bracing apparatus responsive to the drive unit.

2. The system of claim 1, wherein the first parallel processor comprises a polynomial processor.

3. The system of claim 1, wherein the second parallel processor comprises a polynomial processor.

4. The system of claim 1, wherein the first parallel processor receives an input signal from the interface circuit.

5. The system of claim 1, wherein the first parallel processor generates a control signal as a function of the input signal.

6. The system of claim 1, wherein the first generator produces a functional electrical stimulation signal.

7. The system of claim 6, wherein the limb is stimulated by applying the functional electrical stimulation signal thereto.

8. The system of claim 1, wherein at least one of the first and second parallel processors includes a first set of processing elements and a second set of processing elements.

9. The system of claim 1, wherein the interface unit includes a switch activated by action of the person's body.

10. The system of claim 1, wherein the interface unit includes a sensor in contact with the person's body.

11. The system of claim 1, wherein the first generator produces a sequence of functional electrical stimulation signals.

* * * * *